(12) United States Patent
Barth et al.

(10) Patent No.: US 7,674,821 B2
(45) Date of Patent: Mar. 9, 2010

(54) N-[(4,5-DIPHENYL-3-ALKYL-2-THIENYL) METHYL]AMINE [AMIDE, SULFONAMIDE, CARBAMATE AND UREA) DERIVATIVES AS CANNABINOID CB1 RECEPTOR ANTAGONISTS

(75) Inventors: Francis Barth, Saint Georges d'Orques (FR); Christian Congy, Saint Gely du Fesc (FR); Jean-Phillipe Ducoux, Combaillaux (FR); Murielle Rinaldi-Carmona, Saint Georges d'Orques (FR)

(73) Assignee: Sanofi-Aventis, Paris (FR)

( * ) Notice: Subject to any disclaimer, the term of this patent is extended or adjusted under 35 U.S.C. 154(b) by 232 days.

(21) Appl. No.: 11/764,378

(22) Filed: Jun. 18, 2007

(65) Prior Publication Data

US 2007/0270470 A1 Nov. 22, 2007

Related U.S. Application Data

(63) Continuation of application No. PCT/FR2005/003219, filed on Dec. 21, 2005.

(30) Foreign Application Priority Data

Dec. 23, 2004 (FR) .................................. 04 13898

(51) Int. Cl.
*A61K 31/381* (2006.01)
*C07D 333/22* (2006.01)

(52) U.S. Cl. ........................................ 514/438; 549/77

(58) Field of Classification Search ................ 514/438; 549/77

See application file for complete search history.

(56) References Cited

FOREIGN PATENT DOCUMENTS

| EP | 0576357 | 12/1993 |
| WO | WO 2005/035488 | 4/2005 |
| WO | WO 2005/073197 | 8/2005 |

OTHER PUBLICATIONS

Palmer, S. L., et. al., Cannabinergic Ligands, Chemistry and Physics of Lipids vol. 121, (2002) pp. 3-19.

*Primary Examiner*—Taofiq A Solola
(74) *Attorney, Agent, or Firm*—Balaram Gupta

(57) ABSTRACT

The invention concerns compounds of formula (I), wherein X, $R_1$, $R_2$, $R_3$, $R_4$ and $R_5$ are as defined herein.

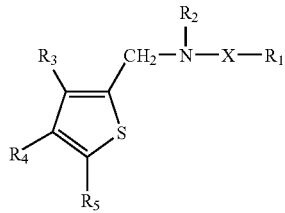

The invention also concerns a method for preparing said compounds and their use as cannabinoid CB1 receptor antagonists.

19 Claims, No Drawings

N-[(4,5-DIPHENYL-3-ALKYL-2-THIENYL) METHYL]AMINE [AMIDE, SULFONAMIDE, CARBAMATE AND UREA) DERIVATIVES AS CANNABINOID CB1 RECEPTOR ANTAGONISTS

CROSS REFERENCE TO RELATED APPLICATIONS

This application is a continuation of International application No. PCT/FR2005/003,219, filed Dec. 21, 2005, which is incorporated herein by reference in its entirety; which claims the benefit of priority of French Patent Application No. 04/13, 898, filed Dec. 23, 2004.

BACKGROUND OF THE INVENTION

1. Field of the Invention

The present invention relates to substituted N-[(4,5-diphenyl-3-alkyl-2-thienyl)methyl]amine derivatives, to their preparation and to their therapeutic use.

2. Description of the Art

Diphenylpyrazole derivatives with affinity for the cannabinoid $CB_1$ receptors have been described especially in patents U.S. Pat. No. 5,624,941, EP 0 576 357, EP 0 656 354, EP 1 150 961 and WO 2005/073197.

4,5-Diarylthiophene derivatives with anti-inflammatory and analgesic properties are described in international patent application WO 91/19708. Thiophene-2-carboxamide derivatives are described in international patent application WO 2005/035488.

All of the references described herein are incorporated herein by reference in their entirety.

SUMMARY OF THE INVENTION

Novel substituted N-[(4,5-diphenyl-3-alkyl-2-thienyl)methyl]amine derivatives have now been found, which have antagonist properties towards the cannabinoid $CB_1$ receptors.

One subject of the present invention is compounds corresponding to the formula:

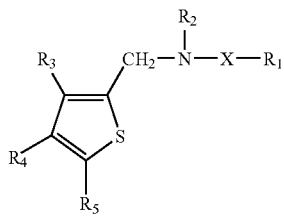

(I)

in which:
X represents a group

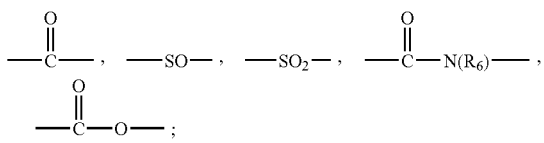

$R_1$ represents:
- a $(C_1-C_7)$alkyl;
- a $(C_3-C_{12})$ non-aromatic carbocyclic radical, which is unsubstituted or substituted one or more times with a $(C_1-C_4)$alkyl;
- a $(C_3-C_7)$cycloalkylmethyl, which is unsubstituted or substituted one or more times on the carbocycle with a $(C_1-C_4)$alkyl;
- an unsubstituted phenyl or a phenyl mono-, di- or trisubstituted with substituents independently chosen from a halogen atom, a $(C_1-C_4)$alkyl, a $(C_1-C_4)$alkoxy, a $(C_1-C_4)$alkylamino, a di$(C_1-C_4)$alkylamino, a cyano, a trifluoromethyl radical, a trifluoromethoxy radical, a group $S(O)_n$Alk, a $(C_1-C_4)$alkylcarbonyl group; or from a phenyl, phenoxy, pyrrolyl, imidazolyl, pyridyl or pyrazolyl radical, the said radicals being unsubstituted or substituted one or more times with a $(C_1-C_4)$alkyl;
- an unsubstituted benzyl or a benzyl mono- or disubstituted on the phenyl with substituents independently chosen from a halogen atom, a $(C_1-C_4)$alkyl, a $(C_1-C_4)$alkoxy or a trifluoromethyl radical, or alpha-substituted with one or two identical or different groups chosen from a $(C_1-C_4)$alkyl and a $(C_3-C_7)$cycloalkyl;
- an unsubstituted phenethyl or a phenethyl mono- or disubstituted on the phenyl with substituents independently chosen from a halogen atom, a $(C_1-C_4)$alkyl, a $(C_1-C_4)$alkoxy and a trifluoromethyl radical;
- a benzhydryl; a benzhydrylmethyl;
- an aromatic heterocyclic radical chosen from a pyrrolyl, an imidazolyl, a furyl, a thienyl, a pyrazolyl or an indolyl, which is unsubstituted or substituted one or more times with substituents independently chosen from a halogen atom, a $(C_1-C_4)$alkyl and a trifluoromethyl radical;

$R_2$ represents a hydrogen atom or a $(C_1-C_3)$alkyl;
$R_3$ represents a $(C_1-C_5)$alkyl or a $(C_3-C_7)$cycloalkyl;
$R_4$ represents an unsubstituted phenyl or a phenyl mono-, di- or trisubstituted with substituents chosen independently from a halogen atom, a $(C_1-C_4)$alkyl, a $(C_1-C_4)$alkoxy, a trifluoromethyl radical and a group $S(O)_n$Alk;
$R_5$ represents an unsubstituted phenyl or a phenyl mono-, di-, or trisubstituted with substituents chosen independently from a halogen atom, a $(C_1-C_4)$alkyl, a $(C_1-C_4)$alkoxy, a trifluoromethyl radical and a group $S(O)_n$Alk;
$R_6$ represents a hydrogen atom or a $(C_1-C_3)$alkyl;
n represents 0, 1 or 2;
Alk represents a $(C_1-C_4)$alkyl.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of hydrates or solvates, i.e. in the form of associations or combinations with one or more water molecules or with a solvent. Such hydrates and solvates also form part of the invention.

DETAILED DESCRIPTION OF THE INVENTION

The term "halogen atom" means a bromine, chlorine, fluorine or iodine atom.

The terms "$(C_1-C_3)$alkyl", "$(C_1-C_4)$alkyl", "$(C_1-C_5)$alkyl" and "$(C_1-C_7)$alkyl" mean, respectively, a linear or branched alkyl radical of one to three carbon atoms, of one to four carbon atoms, of one to five carbon atoms or of one to seven carbon atoms, respectively, such as a methyl, ethyl, propyl, isopropyl, butyl, isobutyl, sec-butyl, tert-butyl, pentyl, isopentyl, hexyl, isohexyl or heptyl radical.

The term "(C$_1$-C$_4$)alkoxy" means a linear or branched alkoxy radical containing from one to four carbon atoms such as a methoxy, ethoxy, propoxy, isopropoxy, butoxy, sec-butoxy or tert-butoxy radical.

The term "(C$_3$-C$_7$)cycloalkyl" means a cyclic alkyl group of 3 to 7 carbon atoms such as a cyclopropyl, cyclobutyl, cyclopentyl, cyclohexyl or cycloheptyl group.

The non-aromatic C$_3$-C$_{12}$ carbocyclic radicals include fused, bridged or spirane monocyclic or polycyclic radicals. The monocyclic radicals include cycloalkyls, for example cyclopropyl, cyclobutyl, cyclopentyl, cyclohexyl, cycloheptyl and cyclooctyl. The fused, bridged or spirane bicyclic or tricyclic radicals include, for example, norbornyl, bornyl, isobornyl, noradamantyl, adamantyl, spiro[5.5]undecyl, bicyclo[2.2.1]heptyl, bicyclo[3.2.1]octyl and bicyclo[3.1.1]heptyl radicals.

Among the compounds of formula (I) that are subjects of the invention, the following are distinguished:
the compounds of formula (IA) in which —X— represents a —CO— radical and the substituents R$_1$ to R$_5$ are as defined for the compounds of formula (I);
the compounds of formula (IB) in which —X— represents an —SO$_2$— radical and the substituents R$_1$ to R$_5$ are as defined for the compounds of formula (I);
the compounds of formula (IC) in which —X— represents a radical —CON(R$_6$)— and the substituents R$_1$ to R$_6$ are as defined for the compounds of formula (I);
the compounds of formula (ID) in which —X— represents a —COO— radical and the substituents R$_1$ to R$_5$ are as defined for the compounds of formula (I);
the compounds of formula (IE) in which —X— represents an —SO— radical and the substituents R$_1$ to R$_5$ are as defined for the compounds of formula (I).

According to the present invention, the compounds of formula (I) that are preferred are those in which:
X represents a group

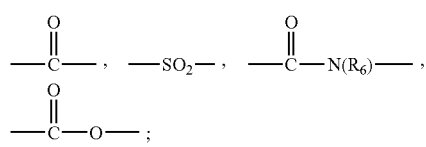

R$_1$ represents:
  a (C$_1$-C$_7$)alkyl;
  a (C$_3$-C$_7$)cycloalkyl which is unsubstituted or substituted one or more times with a (C$_1$-C$_3$)alkyl group;
  a (C$_3$-C$_7$)cycloalkylmethyl which is unsubstituted or substituted one or more times on the carbocycle with a (C$_1$-C$_3$)alkyl;
  a phenyl which is unsubstituted or mono-, di- or trisubstituted with substituents chosen independently from a halogen atom, a (C$_1$-C$_4$)alkyl, a (C$_1$-C$_4$)alkoxy, a cyano, a trifluoromethyl radical, a trifluoromethoxy radical, a group S(O)$_n$Alk, a (C$_1$-C$_4$)alkylcarbonyl group and a phenyl;
  a benzyl which is unsubstituted or mono- or disubstituted with substituents chosen independently from a halogen atom, a (C$_1$-C$_4$)alkyl, a (C$_1$-C$_4$)alkoxy and a trifluoromethyl radical;
  an indolyl;
R$_2$ represents a hydrogen atom or a (C$_1$-C$_3$)alkyl;
R$_3$ represents a (C$_1$-C$_5$)alkyl or a (C$_3$-C$_7$)cycloalkyl;
R$_4$ represents a phenyl which is unsubstituted or mono-, di- or trisubstituted with substituents chosen independently from a halogen atom, a (C$_1$-C$_4$)alkyl, a (C$_1$-C$_4$)alkoxy, a trifluoromethyl radical and a group S(O)$_n$Alk;
R$_5$ represents a phenyl which is unsubstituted or mono-, di- or trisubstituted with substituents chosen independently from a halogen atom, a (C$_1$-C$_4$)alkyl, a (C$_1$-C$_4$)alkoxy, a trifluoromethyl radical and a group S(O)$_n$Alk;
R$_6$ represents a hydrogen atom or a (C$_1$-C$_3$)alkyl;
n represents 0, 1 or 2;
Alk represents a (C$_1$-C$_4$)alkyl, in base form and also in hydrate or solvate form.

Among the compounds of formula (I) that are subjects of the invention, a first group of compounds consists of the compounds for which:
X represents a —CO— group, an —SO$_2$— group, an —SO— group or a —CON(CH$_2$CH$_3$)— group;
R$_1$ represents:
  a 1-ethylpropyl; a 1-methylpentyl; a tert-butyl; an ethyl; a cycloheptyl; a 1-methylcyclopropyl;
  a 3-(trifluoromethyl)phenyl;
  a 4-(trifluoromethyl)phenyl;
and/or R$_2$ represents a hydrogen atom;
and/or R$_3$ represents a methyl;
and/or R$_4$ represents a 4-bromophenyl; a 4-chlorophenyl;
and/or R$_5$ represents a 2,4-dichlorophenyl;

and also the hydrates or solvates thereof.

Among the compounds of the latter group, mention may be made of the compounds of formula (I) for which:
X represents a —CO— group, an —SO$_2$— group; an —SO— group or a —CON(CH$_2$CH$_3$)— group;
R$_1$ represents:
  a 1-ethylpropyl; a 1-methylpentyl; a tert-butyl; an ethyl; a cycloheptyl; a 1-methylcyclopropyl;
  a 3-(trifluoromethyl)phenyl; a 4-(trifluoromethyl)phenyl;
R$_2$ represents a hydrogen atom;
R$_3$ represents a methyl;
R$_4$ represents a 4-bromophenyl; a 4-chlorophenyl;
R$_5$ represents a 2,4-dichlorophenyl;

and also the hydrates or solvates thereof.

Among the compounds of the latter group, mention may be made of the compounds of formula (I) for which:
X represents a —CO— group or an —SO$_2$— group;
R$_1$ represents:
  a 1-ethylpropyl; a 1-methylpentyl;
  a cycloheptyl;
  a 3-(trifluoromethyl)phenyl;
R$_2$ represents a hydrogen atom;
R$_3$ represents a methyl;
R$_4$ represents a 4-bromophenyl;
R$_5$ represents a 2,4-dichlorophenyl;

and also the hydrates or solvates thereof.

Among the compounds of formula (I) that are subjects of the invention, mention may be made especially of the following compounds:
N-[[4-(4-bromophenyl)-5-(2,4-dichlorophenyl)-3-methyl-2-thienyl]methyl]-2-ethylbutanamide;
N-[[4-(4-bromophenyl)-5-(2,4-dichlorophenyl)-3-methyl-2-thienyl]methyl]cycloheptanecarboxamide;
N-[[4-(4-bromophenyl)-5-(2,4-dichlorophenyl)-3-methyl-2-thienyl]methyl]-3-(trifluoromethyl)benzenesulfonamide;
N-[[4-(4-bromophenyl)-5-(2,4-dichlorophenyl)-3-methyl-2-thienyl]methyl]-2-methylhexanamide;
N-[[4-(4-chlorophenyl)-5-(2,4-dichlorophenyl)-3-methyl-2-thienyl]methyl]-2,2-dimethylpropanamide.

N-[[4-(4-chlorophenyl)-5-(2,4-dichlorophenyl)-3-methyl-2-thienyl]methyl]-2-ethylbutanamide.
N-[[4-(4-chlorophenyl)-5-(2,4-dichlorophenyl)-3-methyl-2-thienyl]methyl]-1-methylcyclopropanecarboxamide.
N-[[4-(4-bromophenyl)-5-(2,4-dichlorophenyl)-3-methyl-2-thienyl]methyl]-4-(trifluoromethyl)benzamide.
N-[[4-(4-chlorophenyl)-5-(2,4-dichlorophenyl)-3-methyl-2-thienyl]methyl]-2-methylpropane-2-sulfinamide.
N-[[4-(4-chlorophenyl)-5-(2,4-dichlorophenyl)-3-methyl-2-thienyl]methyl]-2-methylpropane-2-sulfonamide.
3-[[4-(4-chlorophenyl)-5-(2,4-dichlorophenyl)-3-methyl-2-thienyl]methyl]-1,1-diethylurea.

and also the hydrates or solvates thereof.

In the text hereinbelow, the term "protecting group Pg" means a group that makes it possible firstly to protect a reactive function such as a hydroxyl or an amine during a synthesis, and secondly to regenerate the intact reactive function at the end of the synthesis. Examples of protecting groups and protection and deprotection methods are given in "Protective Group in Organic Synthesis", Green et al., 2nd Edition (John Wiley & Sons, Inc., New York), 1991.

In the text hereinbelow, the term "leaving group" means a group that can be readily cleaved from a molecule by breaking a heterolytic bond, with loss of an electron pair. This group may thus be readily replaced with another group during a substitution reaction, for example. Such leaving groups are, for example, halogens or an activated hydroxyl group such as a methanesulfonate, benzenesulfonate, p-toluenesulfonate, triflate, acetate, etc. Examples of leaving groups and references for preparing them are given in "Advances in Organic Chemistry", J. March, 3rd Edition, Wiley Interscience, 1985, p. 310-316.

In accordance with the invention, the compounds of formula (I) may be prepared according to a process that is characterized in that:

a compound of formula:

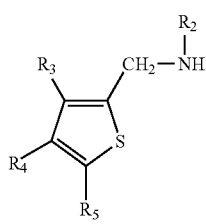

(II)

in which $R_2$, $R_3$, $R_4$ and $R_5$ are as defined for a compound of formula (I), is treated:

either with an acid or a functional derivative of this acid of formula:

HOOC—$R_1$ (III)

in which $R_1$ is as defined for a compound of formula (I), when a compound of formula (I) is to be prepared in which —X— represents a —CO— group;

or with a sulfonyl halide of formula:

Hal-SO$_2$—$R_1$ (IV)

in which $R_1$ is as defined for a compound of formula (I) and Hal represents a halogen atom, preferentially chlorine, when a compound of formula (I) is to be prepared in which —X— represents an —SO$_2$— group;

or with a haloformate of formula:

HalCOOAr (V)

in which Hal represents a halogen atom and Ar represents a phenyl or a 4-nitrophenyl, to give an intermediate compound of formula:

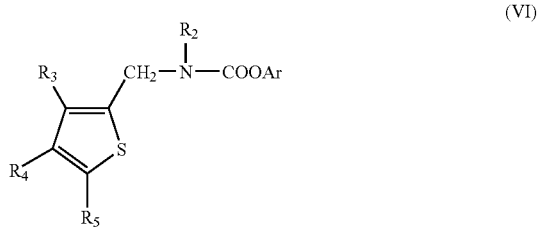

(VI)

in which $R_2$, $R_3$, $R_4$ and $R_5$ are as defined for a compound of formula (I), which is then reacted with an amine of formula:

HN($R_6$)$R_1$ (VII)

in which $R_1$ and $R_6$ are as defined for a compound of formula (I), when a compound of formula (I) is to be prepared in which —X— represents a group —CON($R_6$)—;

or with a haloformate of formula:

HalCOO—$R_1$ (XXIV)

in which Hal represents a halogen atom and $R_1$ is as defined for a compound of formula (I), when a compound of formula (I) is to be prepared in which —X— represents a —COO— group, or with a sulfinyl halide of formula:

Hal-SO—$R_1$ (XXV)

in which $R_1$ is as defined for a compound of formula (I) and Hal represents a halogen atom, when a compound of formula (I) is to be prepared in which —X— represents an —SO— group.

When a compound of formula (II) is treated with the acid of formula (III) itself, the process is performed in the presence of a coupling agent used in peptide chemistry, such as 1,3-dicyclohexylcarbodiimide or benzotriazol-1-yloxytris(dimethylamino)phosphonium hexafluorophosphate or benzotriazol-1-yloxy-tris(pyrrolidino)phosphonium hexafluorophosphate or 2-(1H-benzotriazol-1-yl)-1,1,3,3-tetramethyluronium tetrafluoroborate, in the presence of a base such as triethylamine, N,N-diisopropylethylamine or 1a 4-dimethylaminopyridine, in a solvent such as dichloromethane, dichloroethane, N-N-dimethylformamide or tetrahydrofuran, at a temperature of between −10° C. and the reflux temperature of the solvent.

A functional derivative of the acid (III) that may be used is the acid chloride, the anhydride, a mixed anhydride, a $C_1$-$C_4$ alkyl ester in which the alkyl is straight or branched, or an activated ester, for example the p-nitrophenyl ester.

Thus, in the process according to the invention, the acid chloride obtained by reacting thionyl chloride or oxalyl chloride with the acid of formula (III) may also be reacted with the compound of formula (II), in a solvent such as a chlorinated solvent (for example dichloromethane, dichloroethane or chloroform), an ether (for example tetrahydrofuran or dioxane) or an amide (for example N,N-dimethylformamide), under an inert atmosphere, at a temperature of between 0° C. and room temperature, in the presence of a tertiary amine such as triethylamine, N-methylmorpholine or pyridine.

One variant consists in preparing the mixed anhydride of the acid of formula (III) by reacting ethyl chloroformate with the acid of formula (III), in the presence of a base such as triethylamine, and in reacting it with the compound of formula (II), in a solvent such as dichloromethane, under an inert atmosphere, at room temperature, in the presence of a base such as triethylamine.

When the compound of formula (II) is treated with a sulfonyl halide of formula (IV), the process is performed in the presence of a base such as triethylamine or diisopropylethylamine, in a solvent such as dichloromethane or tetrahydrofuran and at a temperature of between room temperature and the reflux temperature of the solvent.

According to one variant of the process, the compounds of formula (I) in which —X— represents an —SO$_2$— group may be prepared by reacting a compound of formula (I) in which —X— represents an —SO— group with an oxidizing agent. An oxidizing agent that may be used is 3-chloroperbenzoic acid, in a solvent such as dichloromethane and at a temperature of between 0° C. and room temperature.

When a compound of formula (II) is treated with a haloformate of formula (V), the process is performed in the presence of a base such as triethylamine, in a solvent such as dichloromethane and at a temperature of between 0° C. and room temperature. The intermediate compound of formula (VI) thus obtained is then reacted with an amine of formula (VII), in a solvent such as dichloromethane, in the presence of a base such as triethylamine and at a temperature of between 0° C. and the reflux temperature of the solvent.

According to one variant of the process, the compounds of formula (I) in which —X— represents a group —CON(R$_6$)— in which R$_6$=H may be prepared by reacting a compound of formula (II) with an isocyanate of formula R$_1$—N=C=O (VIII), in the presence of a base such as triethylamine, in a solvent such as dichloromethane and at a temperature of between room temperature and the reflux temperature of the solvent.

According to another variant of the process, the compounds of formula (I) in which —X— represents a group —CON(R$_6$)— may be prepared by reacting a compound of formula (II) with a compound of formula ClCON(R$_6$)R$_1$ (IX) in the presence of a base such as triethylamine or 4-dimethylaminopyridine, in a solvent such as dichloromethane and at a temperature of between 0° C. and the reflux temperature of the solvent.

When a compound of formula (II) is treated with a haloformate of formula (XXIV), the process is performed in the presence of a base such as triethylamine, in a solvent such as dichloromethane and at a temperature of between 0° C. and the reflux temperature of the solvent.

When a compound of formula (II) is treated with a sulfinyl halide of formula (XXV), the process is performed in the presence of a base such as triethylamine, in a solvent such as dichloromethane and at a temperature of between room temperature and the reflux temperature of the solvent.

According to another variant of the process, a compound of formula (I) in which R$_2$ represents a (C$_1$-C$_3$)alkyl may be prepared by reacting a compound of formula (I) in which R$_2$=H with a (C$_1$-C$_3$)alkyl halide, in the presence of a base such as sodium hydride, in a solvent such as N,N-dimethylformamide and at a temperature of between room temperature and the reflux temperature of the solvent.

The compounds of formula (I) thus obtained may be subsequently separated from the reaction medium and purified according to standard methods, for example by crystallization or chromatography.

The compounds of formula (II) are prepared by reacting a compound of formula:

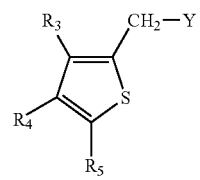

(X)

in which R$_3$, R$_4$ and R$_5$ are as defined for a compound of formula (I) and Y represents a leaving group as defined above, preferably a halogen atom or an activated hydroxyl group such as a methanesulfonate, benzenesulfonate, p-toluenesulfonate or triflate group, with a compound of formula:

in which R$_2$ is as defined for a compound of formula (I).

The reaction is performed in a solvent such as N,N-dimethylformamide, acetonitrile, dichloromethane, toluene or 2-propanol, and in the presence or absence of a base. When a base is used, it is chosen from organic bases such as triethylamine, N,N-diisopropylethylamine or N-methylmorpholine. The reaction is performed at a temperature of between 0° C. and the reflux temperature of the solvent.

According to one variant, a compound of formula (II) in which R$_2$=H may also be prepared by reacting a compound of formula (X) in which Y=Cl with 1,3,5,7-tetraazatricyclo[3.3.1$^{3,7}$]decane (or hexamethylenetetramine), followed by hydrolysis with a strong acid such as hydrochloric acid.

According to another variant, a compound of formula (II) in which R$_2$=H may also be prepared by reducing a compound of formula:

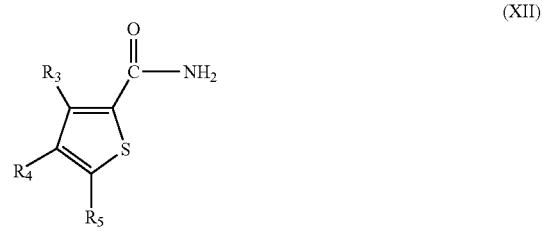

(XII)

in which R$_3$, R$_4$ and R$_5$ are as defined for a compound of formula (I). The reaction is performed using a reducing agent such as borane in a solvent such as tetrahydrofuran, at a temperature of between room temperature and the reflux temperature of the solvent, followed by an acid hydrolysis.

The compounds of formula (III) are known.

The compounds of formula (IV) are commercially available or described in the literature, or may be prepared according to methods described therein such as in J. Org. Chem. USSR, 1970, 6, 2454-2458; J. Am. Chem. Soc., 1952, 74, 2008; J. Med. Chem., 1977, 20(10), 1235-1239; EP 0 469 984; WO 95/18105.

For example, the compounds of formula (IV) may be prepared by halogenation of the corresponding sulfonic acids or salts thereof, for example the sodium or potassium salts thereof. The reaction is preformed in the presence of a halogenating agent such as phosphorus oxychloride, thionyl chloride, phosphorus trichloride, phosphorus tribromide or phosphorus pentachloride, without solvent or in a solvent such as a halogenated hydrocarbon or N,N-dimethylformamide and at a temperature of between −10° C. and 200° C.

The compounds of formulae (V), (VII), (VIII) and (IX) are known or are prepared according to known methods.

The compounds of formula (X) are prepared from compounds of formula:

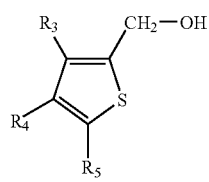

(XIII)

in which $R_3$, $R_4$ and $R_5$ are as defined for a compound of formula (I), according to the standard methods mentioned above.

Thus, for example, when, in a compound of formula (X), Y represents a halogen atom, a compound of formula (XIII) is treated with a halogenating agent such as $PCl_5$, $PBr_3$, HBr or $BBr_3$, in a solvent such as dichloromethane and at a temperature of between 0° C. and room temperature.

When, in a compound of formula (X), Y represents a methanesulfonate, a benzenesulfonate, a p-toluenesulfonate or a trifluoromethanesulfonate, a compound of formula (XIII) is reacted with a sulfonyl chloride of formula W—$SO_2$—Cl in which W represents a methyl, a phenyl, a p-tolyl or a trifluoromethyl. The reaction is performed in the presence of a base such as triethylamine, pyridine or N,N-diisopropylethylamine, in a solvent such as dichloromethane or toluene and at a temperature of between −20° C. and the reflux temperature of the solvent.

The compounds of formula (XI) are known.

The compounds of formula (XII) are prepared by reacting an acid or a functional derivative of this acid of formula:

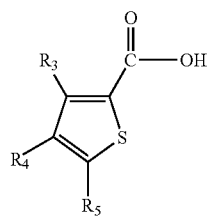

(XIV)

in which $R_3$, $R_4$ and $R_5$ are as defined for a compound of formula (I), with aqueous ammonia according to the methods described above for the reaction of a compound (II) with a compound (III).

The compounds of formula (XIII) are prepared via a reduction reaction of the compounds of formula:

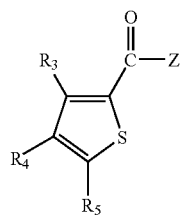

(XV)

in which $R_3$, $R_4$ and $R_5$ are as defined for a compound of formula (I) and Z represents a hydroxyl or a $(C_1$-$C_2)$alkoxy.

The reaction is performed in the presence of a reducing agent such as sodium borohydride or lithium aluminum hydride, in a solvent such as tetrahydrofuran, and at a temperature of between −20° C. and room temperature. When a compound of formula (XV) in which Z=OH is reduced, the acid may be preactivated by reaction with ethyl chloroformate in the presence of triethylamine.

The compounds of formula (XIV) or the compounds of formula (XV) in which Z=OH are prepared via standard hydrolysis of a compound of formula (XV) in which Z=($C_1$-$C_2$)alkoxy.

The reaction is performed via hydrolysis in alkaline medium using, for example, an alkali metal hydroxide such as sodium hydroxide or potassium hydroxide in a solvent such as water, methanol, 1,2-dimethoxyethane, 1,4-dioxane or a mixture of these solvents and at a temperature of between 0° C. and the reflux temperature of the solvent.

The compounds of formula (XV) in which Z=($C_1$-$C_2$)alkoxy are prepared according to Scheme I below in which Hal represents a halogen atom, preferably bromine.

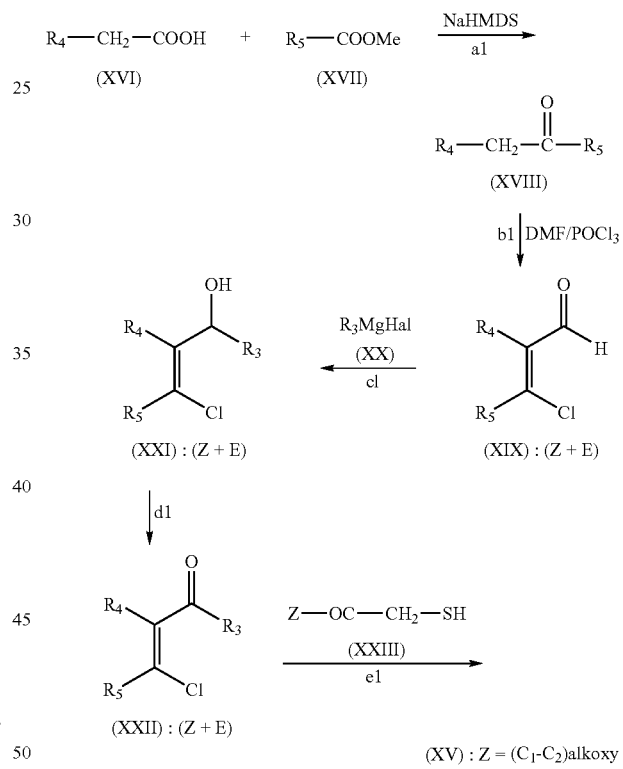

In step a1 of Scheme I, the reaction of a compound of formula (XVI) with a compound of formula (XVII) is performed in the presence of an alkali metal salt of hexamethyldisilazane, for example such as the sodium salt, in a solvent such as tetrahydrofuran and at a temperature of between −70° C. and 0° C.

In step b1, the compound of formula (XVIII) thus obtained is reacted with an N,N-dimethylformamide/phosphorus oxychloride mixture, in a solvent such as 1,2-dichloroethane and at a temperature of between −10° C. and the reflux temperature of the solvent.

The compound of formula (XIX) thus obtained is reacted in step c1 with a $(C_1$-$C_3)$alkylmagnesium halide or a $(C_3$-$C_7)$ cycloalkylmagnesium halide, in a solvent such as tetrahydrofuran and at a temperature of between −20° C. and room temperature.

The compound of formula (XXI) thus obtained is oxidized in step d1 in the presence of an oxidizing agent such as pyridinium dichromate and molecular sieves, in a solvent such as dichloromethane and at room temperature.

The compound (XXII) thus obtained is reacted in step c1 with compound (XXIII), in the presence of a base such as 1,8-diazabicyclo[5.4.0]undec-7-ene, in a solvent such as acetonitrile and at a temperature of between room temperature and the reflux temperature of the solvent.

The compounds of formulae (XVI), (XVII), (XX), (XXIII), (XXIV) and (XXV) are known or prepared according to known methods.

The EXAMPLES below describe the preparation of certain compounds in accordance with the invention. These are non-limiting examples and serve merely to illustrate the present invention. The numbers of the compounds given as examples refer to those given in TABLE I below, which illustrates the chemical structures and the physical properties of a number of compounds according to the invention.

In the Preparations and in the Examples, the following abbreviations are used:
ether: diethyl ether
iso ether: diisopropyl ether
DMSO: dimethyl sulfoxide
DMF: N,N-dimethylformamide
THF: tetrahydrofuran
TBTU: 2-(1H-benzotriazol-1-yl)-1,1,3,3-tetramethyluronium tetrafluoroborate
DCM: dichloromethane
EtOAc: ethyl acetate
DIPEA: diisopropylethylamine
DBU: 1,8-diazabicyclo[5.4.0]undec-7-ene
TFA: trifluoroacetic acid
2N hydrochloric ether: 2N solution of hydrogen chloride in diethyl ether
m.p.: melting point
RT: room temperature
b.p.: boiling point
HPLC: high performance liquid chromatography
Silica H: 60 H silica gel sold by Merck (Darmstadt)
pH 2 buffer solution: solution of 16.66 g of $KHSO_4$ and 32.32 g of $K_2SO_4$ in 1 liter of water.

The proton nuclear magnetic resonance ($^1H$ NMR) spectra are recorded at 200 MHz in DMSO-$d_6$. The chemical shifts δ are expressed in parts per million (ppm). For the interpretation of the spectra, the following abbreviations are used: s: singlet, d: doublet, t: triplet, q: quartet, m: unresolved complex, mt: multiplet, bs: broad singlet, dd: doubled doublet.

The compounds according to the invention are analyzed by LC/UV/MS coupling (liquid chromatography/UV detection/mass spectrometry). The molecular peak (MH$^+$) and the retention time (rt) in minutes are measured.

Method 1:
A Symmetry C18 2.1×50 mm, 3.5 μm column is used, at 30° C., flow rate 0.4 ml/minute.
The eluent is composed as follows:
solvent A: 0.005% trifluoroacetic acid (TFA) in water at pH 3.15;
solvent B: 0.005% TFA in acetonitrile.
Gradient:

| Time (minutes) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is performed at λ=210 nm and the mass detection is performed in positive ESI chemical ionization mode.

Method 2:
An XTerra MS C18 2.1×50 mm, 3.5 μm column is used, at 30° C., flow rate 0.4 ml/minute.
The eluent is composed as follows:
solvent A: 10 mM ammonium acetate (NH$_4$AcO) in water at pH 7;
solvent B: acetonitrile.
Gradient:

| Time (minutes) | % A | % B |
|---|---|---|
| 0 | 100 | 0 |
| 10 | 10 | 90 |
| 15 | 10 | 90 |
| 16 | 100 | 0 |
| 20 | 100 | 0 |

The UV detection is performed at λ=220 nm and the mass detection is performed in positive ESI chemical ionization mode.

PREPARATIONS

1. Preparation of the Compounds of Formula (XVIII):

Preparation 1.1

2-(4-Bromophenyl)-1-(2,4-dichlorophenyl)ethanone (XVIII):

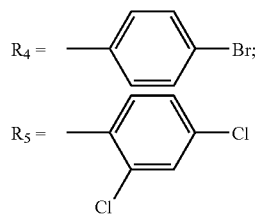

436 ml of a 2M solution of the sodium salt of hexamethyldisilazane in THF are cooled to −60° C., under a nitrogen atmosphere, 400 ml of THF are added, followed by dropwise addition of a solution of 75 g of 4-bromophenylacetic acid in 100 ml of THF, and the mixture is stirred for 1 hour 30 minutes at −70° C. 67.9 g of methyl 2,4-dichlorobenzoate are then added dropwise and the mixture is stirred for 30 minutes and then allowed to warm to 5° C. The reaction mixture is poured into a mixture of ice/1 liter of 2N HCl and extracted with ether, the organic phase is washed with saturated NaHCO$_3$ solution and with water, and dried over Na$_2$SO$_4$, the solvent is evaporated off under vacuum to a volume of 200 ml, pentane is added and the crystalline product formed is filtered off by suction. 80 g of the expected compound are obtained.

Preparation 1.2

2-(4-Chlorophenyl)-1-(2,4-dichlorophenyl)ethanone (XVIII):

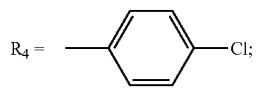

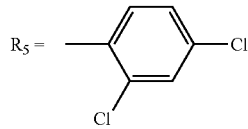

417 ml of a 2M solution of the sodium salt of hexamethyldisilazane in THF are cooled to −60° C., under a nitrogen atmosphere, 350 ml of THF are added, followed by dropwise addition of a solution of 57 g of 4-chlorophenylacetic acid in 70 ml of THF and the mixture is stirred for 2 hours while allowing the temperature to rise to −40° C. The reaction mixture is cooled to −60° C., 65.3 g of methyl 2,4-dichlorobenzoate are added dropwise and the mixture is stirred while allowing the temperature to rise to 0° C. The reaction mixture is poured into a mixture of ice/1 liter of 2N HCl and extracted with ether, the organic phase is dried over $Na_2SO_4$ and the solvent is concentrated under vacuum to a volume of 150 ml. The remaining solution is poured into 300 ml of pentane and the crystalline product formed is filtered off by suction. 60 g of the expected compound are obtained.

2. Preparation of the Compounds of Formula (XIX):

Preparation 2.1

2-(4-Bromophenyl)-3-chloro-3-(2,4-dichlorophenyl) acrylaldehyde (XIX):

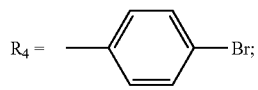

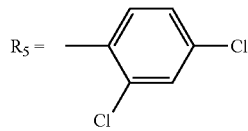

A solution of 33.7 ml of DMF in 75 ml of 1,2-dichloroethane is cooled to −50° C., 40.6 ml of $POCl_3$ are added dropwise and the mixture is then stirred while allowing the temperature to return to RT. A solution of 40 g of the compound obtained in Preparation 1.1 in 300 ml or 1,2-dichloroethane is then added and the mixture is refluxed for 48 hours. After cooling, the reaction mixture is poured into 1.5 liters of ice/water, the pH is brought to 7 by addition of $NaHCO_3$, the resulting mixture is extracted with DCM, the organic phase is dried over $Na_2SO_4$ and the solvent is evaporated off under vacuum. The residue is chromatographed on silica gel, eluting with a gradient of a heptane/DCM mixture of from (90/10; v/v) to (50/50; v/v). 39 g of the expected compound are obtained.

Preparation 2.2

3-Chloro-2-(4-chlorophenyl)-3-(2,4-dichlorophenyl) acrylaldehyde (XIX):

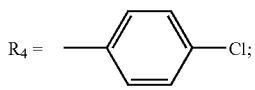

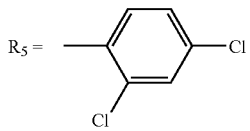

A solution of 54.5 ml of DMF in 80 ml of 1,2-dichloroethane is cooled to 0° C., 60.7 ml of $POCl_3$ are added dropwise and the mixture is then stirred while allowing the temperature to return to RT. A solution of 30 g of the compound of Preparation 1.2 in 300 ml of 1,2-dichloroethane is then added and the mixture is heated at 80° C. for 4 hours. After cooling, the reaction mixture is poured onto ice, the pH is brought to 7 by adding sodium acetate, the resulting mixture is extracted with DCM, the organic phase is dried over $Na_2SO_4$ and the solvent is evaporated off under vacuum. The residue is chromatographed on silica gel, eluting with DCM. 35 g of the expected compound are obtained.

3. Preparation of the Compounds of Formula (XXI):

Preparation 3.1

3-(4-Bromophenyl)-4-chloro-4-(2,4-dichlorophenyl) but-3-en-2-ol (XXI):

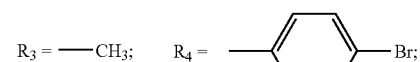

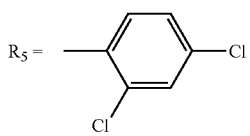

A solution of 10 g of the compound obtained in Preparation 2.1 in 100 ml of THF is cooled to −20° C. and 25 ml of a 1.4M solution of methylmagnesium bromide in THF are added dropwise. The reaction mixture is poured into saturated NH$_4$Cl solution and extracted with ether, the organic phase is dried over Na$_2$SO$_4$ and the solvent is evaporated off under vacuum. 11 g of the expected compound are obtained.

Preparation 3.2

4-Chloro-3-(4-chlorophenyl)-4-(2,4-dichlorophenyl) but-3-en-2-ol (XXI):

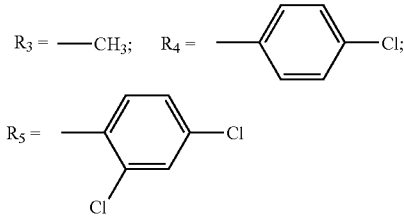

A solution of 35 g of the compound obtained in Preparation 2.2 in 200 ml of THF is cooled to −20° C. and 54.2 ml of a 1.4M solution of methylmagnesium bromide in THF are added dropwise. The reaction mixture is poured into saturated NH$_4$Cl solution and extracted with ether, the organic phase is dried over Na$_2$SO$_4$ and the solvent is evaporated off under vacuum. The residue is chromatographed on silica gel, eluting with heptane and then with a heptane/EtOAc mixture up to (80/20; v/v). 16 g of the expected compound are obtained.

4. Preparation of the Compounds of Formula (XXII):

Preparation 4.1

3-(4-Bromophenyl)-4-chloro-4-(2,4-dichlorophenyl) but-3-en-2-one (XXII):

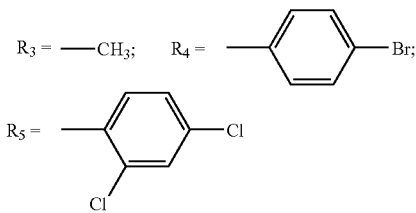

A mixture of 7 g of the compound obtained in Preparation 3.1, 12.8 g of pyridinium dichromate and 15 g of 4 Å molecular sieves in 200 ml of DCM is stirred for 24 hours at RT. The reaction mixture is filtered through Celite and the filtrate is concentrated under vacuum. The residue is chromatographed on silica gel, eluting with heptane and then with a heptane/EtOAc mixture (96/4; v/v). 7 g of the expected compound are obtained.

Preparation 4.2

4-Chloro-3-(4-chlorophenyl)-4-(2,4-dichlorophenyl) but-3-en-2-one (XXII):

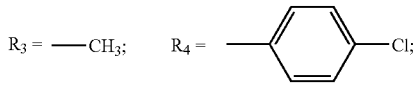

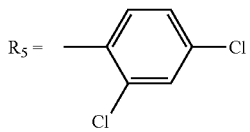

A mixture of 16 g of the compound obtained in Preparation 3.2, 41.6 g of pyridinium dichromate and 40 g of 4 Å molecular sieves in 200 ml of DCM is stirred overnight at room temperature. The reaction mixture is filtered through Celite and the filtrate is concentrated under vacuum. The residue is chromatographed on silica gel, eluting with a heptane/EtOAc mixture (90/10; v/v). 15 g of the expected compound are obtained.

5. Preparation of the Compounds of Formula (XV):

Preparation 5.1

Methyl 4-(4-bromophenyl)-5-(2,4-dichlorophenyl)- 3-methylthiophene-2-carboxylate (XV):

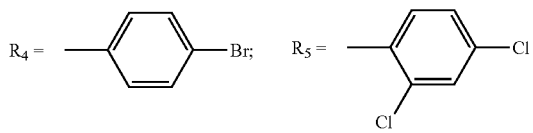

To a solution of 2.7 g of the compound obtained in Preparation 4.1 in 25 ml of acetonitrile are added 1.49 ml of methyl mercaptoacetate and then 2.4 ml of DBU, and the mixture is stirred overnight at RT. The reaction mixture is poured into 12.5 ml of 1N HCl and extracted with EtOAc, the organic phase is washed with water and dried over Na$_2$SO$_4$, and the solvent is evaporated off under vacuum. The residue is chromatographed on silica gel, eluting with a heptane/EtOAc mixture (95/5; v/v). 1.21 g of the expected compound are obtained.

Preparation 5.2

Methyl 4-(4-chlorophenyl)-5-(2,4-dichlorophenyl)-3-methylthiophene-2-carboxylate

(XV):

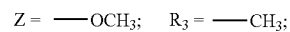

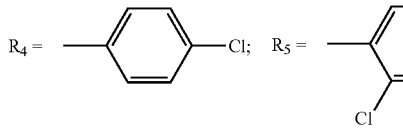

A mixture of 7.5 g of the compound obtained in Preparation 4.2 and 4.4 g of methyl mercaptoacetate is heated to 80° C., 3 ml of DBU are added dropwise and the mixture is stirred overnight at 60° C. The reaction mixture is concentrated under vacuum, the residue is taken up in 1N HCl solution and extracted with an ether/EtOAc mixture, the organic phase is dried over $Na_2SO_4$ and the solvents are evaporated off under vacuum. The residue is chromatographed on silica gel, eluting with heptane and then with a heptane/EtOAc mixture up to (90/10; v/v). 3.5 g of the expected compound are obtained after crystallization from MeOH.

6. Preparation of the Compounds of Formula (XIV):

Preparation 6.1

4-(4-Bromophenyl)-5-(2,4-dichlorophenyl)-3-methylthiophene-2-carboxylic acid

(XIV):

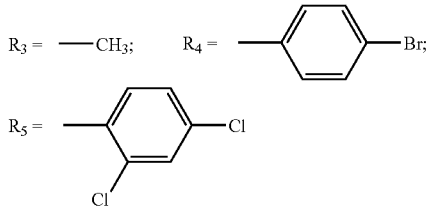

To a solution of 1.21 g of the compound obtained in Preparation 5.1 in 6 ml of 1,2-dimethoxyethane are added 3 ml of MeOH and then 1.73 ml of 30% NaOH solution, and the mixture is stirred for 24 hours at 50° C. The reaction mixture is concentrated under vacuum, the residue is taken up in water, the aqueous phase is washed with ether, acidified to pH 2 by adding concentrated HCl solution and extracted with ether, the organic phase is dried over $Na_2SO_4$ and the solvent is evaporated off under vacuum. 0.75 g of the expected compound is obtained after crystallization from a pentane/iso ether mixture (75/25; v/v).

Preparation 6.2

4-(4-Chlorophenyl)-5-(2,4-dichlorophenyl)-3-methylthiophene-2-carboxylic acid

(XIV):

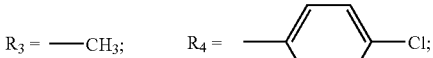

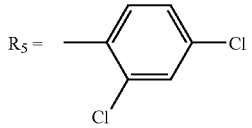

To a solution of 3.5 g of the compound obtained in Preparation 5.2 in 15 ml of 1,2-dimethoxyethane are added 15 ml of MeOH and then 0.68 g of NaOH pellets, and the mixture is stirred overnight at room temperature and then heated at 60° C. for 3 hours. The reaction mixture is concentrated under vacuum, the residue is taken up in water, washed with ether, acidified to pH 2 by adding concentrated HCl solution and extracted with ether, the organic phase is dried over $Na_2SO_4$ and the solvent is evaporated off under vacuum. 3 g of the expected compound are obtained after crystallization from a DCM/iso ether mixture.

7. Preparation of the Compounds of Formula (XII):

Preparation 7.1

4-(4-Bromophenyl)-5-(2,4-dichlorophenyl)-3-methylthiophene-2-carboxamide

(XII):

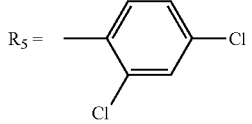

A mixture of 3 g of the compound obtained in Preparation 6.1 and 1.98 ml of thionyl chloride in 60 ml of 1,2-dichloroethane is heated at 70° C. for 4 hours. The reaction mixture is concentrated under vacuum, the residue is taken up in 1,2-dichloroethane and the solvent is evaporated off under vacuum to give 3 g of the acid chloride. A solution of 6.51 ml of 2M aqueous ammonia in MeOH and 1.37 ml of triethylamine in 10 ml of DCM is cooled to 50° C., a solution of 3 g of the acid chloride in 5 ml of DCM is added dropwise and the mixture is stirred overnight while allowing the temperature to return to RT. The reaction mixture is concentrated under vacuum, the residue is taken up in water and extracted with EtOAc, the organic phase is dried over $Na_2SO_4$ and the solvent is evaporated off under vacuum. 2.5 g of the expected compound are obtained after crystallization from an ether/iso ether mixture.

Preparation 7.2

4-(4-Chlorophenyl)-5-(2,4-dichlorophenyl)-3-methylthiophene-2-carboxamide (XII):

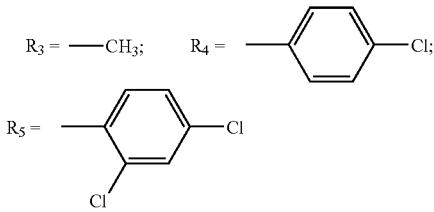

$R_3 =$ —$CH_3$;    $R_4 =$ ⟨phenyl⟩—Cl;

$R_5 =$ ⟨dichlorophenyl⟩

A mixture of 3 g of the compound obtained in Preparation 6.2 and 2.2 ml of thionyl chloride in 60 ml of 1,2-dichloroethane is refluxed for 2 hours 30 minutes. The reaction mixture is concentrated under vacuum, the residue is taken up in 1,2-dichloroethane and the solvent is evaporated off under vacuum to give 3 g of the acid chloride. A solution of 7.21 ml of 2M aqueous ammonia in MeOH and 1.52 ml of triethylamine in 20 ml of DCM is cooled to 0° C., a solution of 3 g of the acid chloride in 20 ml of DCM is added dropwise and the mixture is stirred overnight while allowing the temperature to return to room temperature. The reaction mixture is concentrated under vacuum, the residue is taken up in water and extracted with ether, the organic phase is dried over $Na_2SO_4$ and the solvent is evaporated off under vacuum. The residue is chromatographed on silica gel, eluting with DCM and then with a DCM/2-propanol mixture up to (95/5; v/v). 2 g of the expected compound are obtained after crystallization from iso ether.

8. Preparation of the Compounds of Formula (II):

Preparation 8.1

1-[4-(4-Bromophenyl)-5-(2,4-dichlorophenyl)-3-methyl-2-thienyl]methanamine hydrochloride (II):

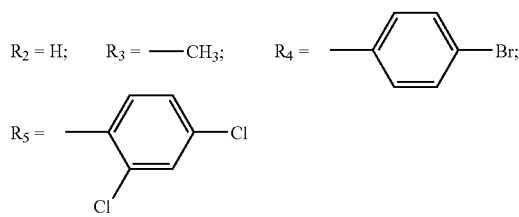

$R_2 = H$;    $R_3 =$ —$CH_3$;    $R_4 =$ ⟨phenyl⟩—Br;

$R_5 =$ ⟨dichlorophenyl⟩

To a solution of 2.5 g of the compound obtained in Preparation 7.1 in 50 ml of THF are added 22.67 ml of a 1M solution of borane in THF, and the mixture is then refluxed for 15 hours. MeOH is then added until the evolution of gas has ceased, and 10 ml of a 2N solution of HCl in ether are added. The reaction mixture is concentrated under vacuum to a volume of 10 ml and then added dropwise, at RT, to 150 ml of iso ether and stirred overnight at RT, and the precipitate formed is filtered off by suction. 1.9 g of the expected compound are obtained.

Preparation 8.2

1-[4-(4-Chlorophenyl)-5-(2,4-dichlorophenyl)-3-methyl-2-thienyl]methanamine hydrochloride (II):

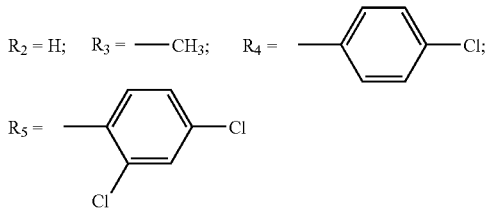

$R_2 = H$;    $R_3 =$ —$CH_3$;    $R_4 =$ ⟨phenyl⟩—Cl;

$R_5 =$ ⟨dichlorophenyl⟩

To a solution of 2 g of the compound obtained in Preparation 7.2 in 20 ml of THF are added 20.2 ml of a 1M solution of borane in THF, and the mixture is then refluxed for 5 hours. MeOH is then added until the evolution of gas has ceased, and 10 ml of a 2N solution of HCl in ether are added and the mixture is stirred for 30 minutes. The reaction mixture is concentrated under vacuum to a volume of 10 ml, which is added dropwise at room temperature to 150 ml of an ether/iso ether mixture (50/50; v/v) and stirred overnight at room temperature, and the precipitate formed is filtered off by suction. 1.5 g of the expected compound are obtained.

EXAMPLE 1

Compound 1

N-[[4-(4-Bromophenyl)-5-(2,4-dichlorophenyl)-3-methyl-2-thienyl]methyl]-2-ethylbutanamide A mixture of 0.35 g of the compound obtained in Preparation 8.1, 0.32 ml of triethylamine and 0.1 g of 2-ethylbutyryl chloride in 20 ml of DCM is stirred for 1 hour at RT. The reaction mixture is concentrated under vacuum, the residue is taken up in water and extracted with EtOAc, the organic phase is dried over $Na_2SO_4$ and the solvent is evaporated off under vacuum. The residue is dissolved in DCM, iso ether is added and the crystalline product formed is filtered off by suction. 0.28 g of the expected compound is obtained.

$MH^+=524$; rt=11.86 (method 2) $^1H$ NMR: DMSO-$d_6$: δ (ppm): 0.8: t: 6H; 1.4: mt: 4H; 1.85-2.15: m: 4H; 4.45: d: 2H; 6.9-7.7: m: 7H; 8.5: t: 1H.

EXAMPLE 2

Compound 2

N-[[4-(4-Bromophenyl)-5-(2,4-dichlorophenyl)-3-methyl-2-thienyl]methyl]cycloheptanecarboxamide A mixture of 0.35 g of the compound obtained in Preparation 8.1, 0.11 g of cycloheptanecarboxylic acid, 0.32 mg of triethylamine and 0.27 g of TBTU in 20 ml of DCM is stirred overnight at RT. The reaction mixture is concentrated under vacuum, the residue is taken up in water and extracted with EtOAc, the organic phase is dried over $Na_2SO_4$ and the solvent is evaporated off under vacuum. The residue is dissolved in DCM, iso ether is added and the crystalline product formed is filtered off by suction. 0.27 g of the expected compound is obtained.

$MH^+$=550; rt=12.4 (method 2) $^1$H NMR: DMSO-$d_6$: δ (ppm): 1.2-1.9: m: 12H; 2.02: s: 3H; 2.3: mt: 1H; 4.4: d: 2H; 6.9-7.7: m: 7H; 8.4: t: 1H.

EXAMPLE 3

Compound 3

N-[[4-(4-Bromophenyl)-5-(2,4-dichlorophenyl)-3-methyl-2-thienyl]methyl]-3-(trifluoromethyl)benzenesulfonamide A mixture of 0.35 g of the compound obtained in Preparation 8.1, 0.2 g of 3-(trifluoromethyl)benzenesulfonyl chloride and 0.32 ml of triethylamine in 20 ml of DCM is stirred overnight at RT. The reaction mixture is concentrated under vacuum, the residue is taken up in water and extracted with EtOAc, the organic phase is washed with water and dried over $Na_2SO_4$, and the solvent is evaporated off under vacuum. The residue is chromatographed on silica gel, eluting with a DCM/EtOAc mixture (90/10; v/v). 0.25 g of the expected compound is obtained.

$MH^+$=632; rt=12.28 (method 2) $^1$H NMR: DMSO-$d_6$: δ (ppm): 1.9: s: 3H; 4.3: s: 2H; 6.7-8.2: m: 11H; 8.65: bs: 1H.

EXAMPLE 4

Compound 4

N-[[4-(4-Bromophenyl)-5-(2,4-dichlorophenyl)-3-methyl-2-thienyl]methyl]-2-methylhexanamide A mixture of 0.35 g of the compound obtained in Preparation 8.1, 0.35 ml of triethylamine, 0.11 g of 2-methylhexanoic acid and 0.29 g of TBTU in 20 ml of DCM is stirred for 48 hours at RT. The reaction mixture is concentrated under vacuum, the residue is taken up in water and extracted with EtOAc, the organic phase is dried over $Na_2SO_4$ and the solvent is evaporated off under vacuum. 0.3 g of the expected compound, which crystallizes, is obtained.

$MH^+$=538; rt=12.71 (method 1) $^1$H NMR: DMSO-$d_6$: δ (ppm): 0.8: t: 3H; 1.0: d: 3H; 1.05-1.65: m: 6H; 2.05: s: 3H; 2.25: mt: 1H; 4.45: mt: 2H; 6.9-7.7: m: 7H; 8.55: t: 1H.

EXAMPLE 5

Compound 5

N-[[4-(4-Chlorophenyl)-5-(2,4-dichlorophenyl)-3-methyl-2-thienyl]methyl]-2,2-dimethylpropanamide A mixture of 0.35 g of the compound obtained in Preparation 8.2, 0.35 ml of triethylamine and 0.11 ml of 2,2-dimethylpropanoyl chloride in 20 ml of DCM is stirred for 2 hours at room temperature. The reaction mixture is concentrated under vacuum, the residue is taken up in water and extracted with ether, the organic phase is dried over $Na_2SO_4$ and the solvent is evaporated off under vacuum. 0.3 g of the expected compound is obtained after crystallization from an ether/iso ether mixture.

$^1$H NMR: DMSO-$d_6$: δ (ppm): 1.12: s: 9H; 2.03: s: 3H; 4.43: d: 2H; 7.07: d: 2H; 7.24-7.40: m: 4H; 7.58: bs: 1H; 8.19: t: 1H.

EXAMPLE 6

Compound 6

N-[[4-(4-Chlorophenyl)-5-(2,4-dichlorophenyl)-3-methyl-2-thienyl]methyl]-2-ethylbutanamide A mixture of 0.35 g of the compound obtained in Preparation 8.2, 0.35 ml of triethylamine and 0.12 g of 2-ethylbutyryl chloride in 20 ml of DCM is stirred for 2 hours at room temperature. The reaction mixture is concentrated under vacuum, the residue is taken up in 0.5 N HCl solution and extracted with ether, the organic phase is dried over $Na_2SO_4$ and the solvent is evaporated off under vacuum. 0.3 g of the expected compound is obtained after crystallization from iso ether.

$^1$H NMR: DMSO-$d_6$: δ (ppm): 0.81: t: 6H; 1.42: mt: 4H; 1.91-2.15: m: 4H; 4.47: d: 2H; 7.07: d: 2H; 7.22-7.44: m: 4H; 7.61: d: 1H; 8.50: t: 1H.

EXAMPLE 7

Compound 7

N-[[4-(4-Chlorophenyl)-5-(2,4-dichlorophenyl)-3-methyl-2-thienyl]methyl]-1-methylcyclopropanecarboxamide A mixture of 0.35 g of the compound obtained in Preparation 8.2, 0.35 ml of triethylamine, 0.09 g of 1-methylcyclopropanecarboxylic acid and 0.3 g of TBTU in 30 ml of DCM is stirred for 12 hours at room temperature. The reaction mixture is concentrated under vacuum, the residue is taken up in water and extracted with ether, the organic phase is dried over $Na_2SO_4$ and the solvent is evaporated off under vacuum. 0.2 g of the expected compound is obtained after crystallization from iso ether.

$^1$H NMR: DMSO-$d_6$: δ (ppm): 0.53: q: 2H; 0.97: q: 2H; 1.27: s: 3H; 2.05: s: 3H; 4.43: d: 2H; 7.07: d: 2H; 7.25-7.43: m: 4H; 7.59: d: 1H; 8.25: t: 1H.

EXAMPLE 8

Compound 8

N-[[4-(4-Bromophenyl)-5-(2,4-dichlorophenyl)-3-methyl-2-thienyl]methyl]-4-(trifluoromethyl)benzamide A mixture of 0.35 g of the compound obtained in Preparation 8.1, 0.17 g of 4-(trifluoromethyl)benzoyl chloride and 0.32 ml of triethylamine in 20 ml of DCM is stirred overnight at room temperature. The reaction mixture is concentrated under vacuum, the residue is taken up in water and extracted with ether, the organic phase is dried over $Na_2SO_4$ and the solvent is evaporated off under vacuum. The residue is chromatographed on silica gel, eluting with heptane and then with a heptane/EtOAc mixture to (90/10; v/v). 0.3 g of the expected compound is obtained.

$^1$H NMR: DMSO-$d_6$: δ (ppm): 2.12: s: 3H; 4.68: d: 2H; 7.02: d: 2H; 7.25-7.41: m: 2H; 7.49: d: 2H; 7.59: d: 1H; 7.87: d: 2H; 8.09: d: 2H; 9.44: t: 1H.

EXAMPLE 9

Compound 9

N-[[4-(4-Chlorophenyl)-5-(2,4-dichlorophenyl)-3-methyl-2-thienyl]methyl]-2-methylpropane-2-sulfinamide A mixture of 0.3 g of the compound obtained in Preparation 8.2, 0.12 g of 2-methylpropane-2-sulfinyl chloride and 0.3 ml of triethylamine in 20 ml of DCM is stirred for 2 hours at room temperature. The reaction mixture is concentrated under vacuum, the residue is taken up in water and extracted with ether, the organic phase is dried over $Na_2SO_4$ and the solvent is evaporated off under vacuum. The residue is chromatographed on silica gel, eluting with DCM and then with a DCM/EtOAc mixture to (90/10; v/v). 0.2 g of the expected compound is obtained.

$^1$H NMR: DMSO-$d_6$: δ (ppm): 1.16: s: 9H; 2.03: s: 3H; 4.36: mt: 2H; 6.03: t: 1H; 7.07: d: 2H; 7.22-7.47: m: 4H; 7.60: d: 1H.

EXAMPLE 10

Compound 10

N-[[4-(4-Chlorophenyl)-5-(2,4-dichlorophenyl)-3-methyl-2-thienyl]methyl]-2-methylpropane-2-sulfonamide A mixture of 0.35 g of Compound 9 and 0.3 g of 3-chloroperbenzoic acid in 20 ml of DCM is stirred for 1 hour at room temperature. 10% $NaHCO_3$ solution is then added, the mixture is extracted with DCM, the organic phase is dried over $Na_2SO_4$ and the solvent is evaporated off under vacuum. The residue is chromatographed on silica gel, eluting with DCM. 0.18 g of the expected compound is obtained after crystallization from iso ether.

$^1$H NMR: DMSO-$d_6$: δ (ppm): 1.30: s: 9H; 2.03: s: 3H; 4.42: d: 2H; 7.08: d: 2H; 7.27-7.44: m: 4H; 7.62: d: 1H; 7.66: t: 1H.

EXAMPLE 11

Compound 11

3-[[4-(4-Chlorophenyl)-5-(2,4-dichlorophenyl)-3-methyl-2-thienyl]methyl]-1,1-diethylurea A mixture of 0.35 g of the compound obtained in Preparation 8.2, 0.165 ml of diethylcarbamic chloride, 0.1 g of 4-dimethylaminopyridine and 0.11 g of $K_2CO_3$ in 30 ml of DCM is heated at 45° C. for 48 hours. The reaction mixture is concentrated under vacuum, the residue is taken up in water and extracted with ether, the organic phase is dried over $Na_2SO_4$ and the solvent is evaporated off under vacuum. The residue is chromatographed on silica gel, eluting with DCM and then with a DCM/MeOH mixture to (97.5/2.5; v/v). 0.25 g of the expected compound is obtained.

$^1$H NMR: DMSO-$d_6$: δ (ppm): 1.03: t: 6H; 2.05: s: 3H; 3.22: q: 4H; 4.41: d: 2H; 6.95: t: 1H; 7.07: d: 2H; 7.24-7.44: m: 4H; 7.59: d: 1H.

The table that follows illustrates the chemical structures of a number of examples of compounds according to the invention.

TABLE I

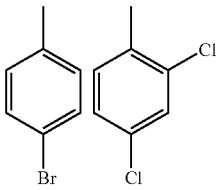

(I)

| Compounds | —X— | $R_1$ | $R_2$ | $R_3$ | $R_4$ | $R_5$ |
|---|---|---|---|---|---|---|
| 1 | —CO— | —CH(CH$_2$CH$_3$)$_2$ | H | —CH$_3$ | 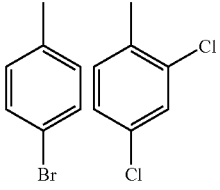 | 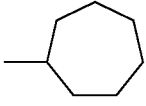 |
| 2 | —CO— | 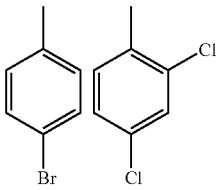 | H | —CH$_3$ | 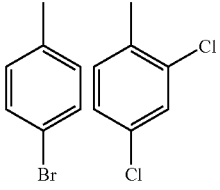 | |

TABLE I-continued (I)

[Structure: thiophene ring with R3, R4, R5 substituents and CH2-N(R2)-X-R1 group]

| Compounds | —X— | R1 | R2 | R3 | R4 | R5 |
|---|---|---|---|---|---|---|
| 3 | —SO2— | 3-(CF3)-phenyl | H | —CH3 | 4-Br-phenyl | 2,4-diCl-phenyl |
| 4 | —CO— | —CH(CH3)(CH2)3—CH3 | H | —CH3 | 4-Br-phenyl | 2,4-diCl-phenyl |
| 5 | —CO— | —C(CH3)3 | H | —CH3 | 4-Cl-phenyl | 2,4-diCl-phenyl |
| 6 | —CO— | —CH(CH2CH3)2 | H | —CH3 | 4-Cl-phenyl | 2,4-diCl-phenyl |
| 7 | —CO— | 1-methylcyclopropyl | H | —CH3 | 4-Cl-phenyl | 2,4-diCl-phenyl |
| 8 | —CO— | 4-(CF3)-phenyl | H | —CH3 | 4-Br-phenyl | 2,4-diCl-phenyl |

TABLE I-continued

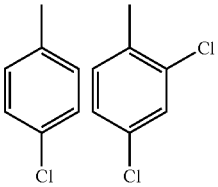

| Compounds | —X— | R₁ | R₂ | R₃ | R₄ | R₅ |
|---|---|---|---|---|---|---|
| 9 | —SO— | —C(CH₃)₃ | H | —CH₃ | 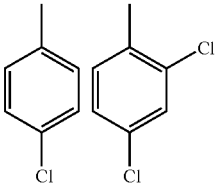 | 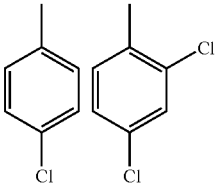 |
| 10 | —SO₂— | —C(CH₃)₃ | H | —CH₃ | 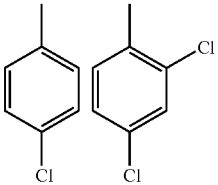 | 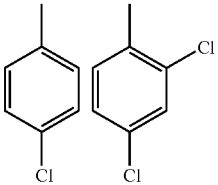 |
| 11 | CH₃CH₂<br>\|<br>—CON— | —CH₂CH₃ | H | —CH₃ | 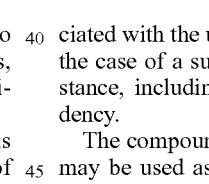 | |

The compounds of formula (I) show very good in vitro affinity ($IC_{50} \leq 5 \times 10^{-7}$ M) for the $CB_1$ cannabinoid receptors, under the experimental conditions described by M. Rinaldi-Carmona et al. (FEBS Letters, 1994, 350, 240-244).

The antagonist nature of the compounds of formula (I) was determined by means of the results obtained in models of inhibition of adenylate cyclase as described in M. Bouaboula et al., J. Biol. Chem., 1995, 270, 13 973-13 980, M. Rinaldi-Carmona et al., J. Pharmacol. Exp. Ther., 1996, 278, 871-878 and M. Bouaboula et al., J. Biol. Chem., 1997, 272, 22 330-22 339.

The toxicity of the compounds of formula (I) is compatible with their use as medicaments.

Thus, according to another of its aspects, a subject of the invention is medicaments comprising a compound of formula (I) or an addition salt thereof with a pharmaceutically acceptable acid, or alternatively a solvate or a hydrate of the compound of formula (I).

Thus, the compounds according to the invention may be used in man or animals in the treatment or prevention of diseases involving the $CB_1$ cannabinoid receptors.

For example, and in a non-limiting manner, the compounds of formula (I) are useful as psychotropic medicaments, especially for treating psychiatric disorders including anxiety, depression, mood disorders, insomnia, delirium disorders, obsessive disorders, psychoses in general, schizophrenia, attention and hyperactivity disorders (AHD) in hyperkinetic children (MBD), and also for the treatment of disorders associated with the use of psychotropic substances, especially in the case of a substance abuse and/or dependency on a substance, including alcohol dependency and nicotine dependency.

The compounds of formula (I) according to the invention may be used as medicaments for treating migraine, stress, diseases of psychosomatic origin, panic attacks, epilepsy, motor disorders, in particular dyskinesia or Parkinson's disease, trembling and dystonia.

The compounds of formula (I) according to the invention may also be used as medicaments in the treatment of memory disorders, cognitive disorders, in particular in the treatment of senile dementia and Alzheimer's disease, and also in the treatment of attention or consciousness disorders. Furthermore, the compounds of formula (I) may be useful as neuroprotective agents, in the treatment of ischemia, cranial trauma and the treatment of neurodegenerative diseases: including chorea, Huntington's chorea and Tourrette's syndrome.

The compounds of formula (I) according to the invention may be used as medicaments in the treatment of pain, neuropathic pain, acute peripheral pain, chronic pain of inflammatory origin.

The compounds of formula (I) according to the invention may be used as medicaments in the treatment of appetite disorders, appetence disorders (for sugars, carbohydrates, drugs, alcohol or any appetizing substance) and/or eating behavioral disorders, especially for the treatment of obesity or bulimia and also for the treatment of type II diabetes or non-insulin-dependent diabetes and for the treatment of dyslipidemia and metabolic syndrome. Thus, the compounds of formula (I) according to the invention are useful in the treatment of obesity and the risks associated with obesity, especially the cardiovascular risks. Furthermore, the compounds of formula (I) according to the invention may be used as medicaments in the treatment of gastrointestinal disorders, diarrhea disorders, ulcers, vomiting, bladder and urinary disorders, disorders of endocrine origin, cardiovascular disorders, hypotension, hemorrhagic shock, septic shock, chronic cirrhosis of the liver, hepatic steatosis, steatohepatitis, asthma, Raynaud's syndrome, glaucoma, fertility disorders, premature interruption of pregnancy, inflammatory phenomena, immune system diseases, in particular autoimmune diseases and neuroinflammatory diseases such as rheumatoid arthritis, reactional arthritis, diseases resulting in demyelinization, multiple sclerosis, infectious and viral diseases such as encephalitis, strokes, and also as medicaments for anticancer chemotherapy, for the treatment of Guillain-Barré syndrome and for the treatment of osteoporosis.

According to the present invention, the compounds of formula (I) are most particularly useful for treating psychotic disorders, in particular schizophrenia, attention and hyperactivity disorders (AHD) in hyperkinetic children (MBD); for treating appetite and obesity disorders; for treating memory and cognitive deficits; for treating alcohol dependency and nicotine dependency, i.e. for weaning from alcohol and for weaning from tobacco.

According to one of its aspects, the present invention relates to the use of a compound of formula (I), pharmaceutically acceptable salts thereof and solvates or hydrates thereof for treating the disorders and diseases indicated above.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, a solvate or a hydrate of the said compound, and also at least one pharmaceutically acceptable excipient.

The said excipients are chosen according to the pharmaceutical form and the desired mode of administration, from the usual excipients known to those skilled in the art.

In the pharmaceutical compositions of the present invention for oral, sublingual subcutaneous, intramuscular, intravenous, topical, local, intratracheal, intranasal, transdermal or rectal administration, the active principle of formula (I) above, or the possible salt, solvate or hydrate thereof, may be administered in a unit form of administration, as a mixture with standard pharmaceutical excipients, to man and animals for the prophylaxis or treatment of the above disorders or diseases.

The appropriate unit forms of administration include oral-route forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, pomades or lotions.

By way of example, a unit form of administration of a compound according to the invention in tablet form may comprise the following components:

| | |
|---|---:|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may be from 0.01 to 100 mg/kg in one or more dosage intakes, preferentially 0.02 to 50 mg/kg.

There may be particular cases in which higher or lower dosages are appropriate; such dosages do not depart from the context of the invention. According to the usual practice, the dosage that is appropriate to each patient is determined by the doctor according to the mode of administration and the weight and response of the said patient.

According to another of its aspects, the present invention also relates to a method for treating the pathologies indicated above, which comprises the administration to a patient of an effective dose of a compound according to the invention, or a pharmaceutically acceptable salt or hydrate or solvate thereof.

What is claimed is:

1. A compound of the formula (I):

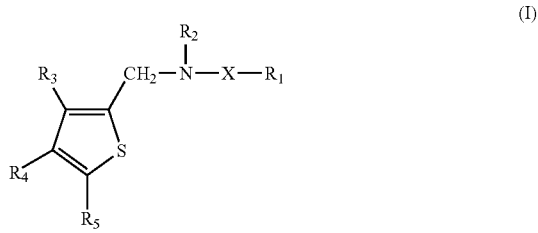

wherein:

X represents a group

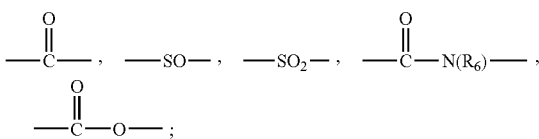

$R_1$ represents:

a $(C_1-C_7)$alkyl;

a $(C_3-C_{12})$ non-aromatic carbocyclic radical, which is unsubstituted or substituted one or more times with a $(C_1-C_4)$alkyl;

a $(C_3-C_7)$cycloalkylmethyl, which is unsubstituted or substituted one or more times on the carbocycle with a $(C_1-C_4)$alkyl;

an unsubstituted phenyl or a phenyl mono-, di- or trisubstituted with substituents independently chosen from a halogen atom, a $(C_1-C_4)$alkyl, a $(C_1-C_4)$alkoxy, a$(C_1-C_4)$alkylamino, a di$(C_1-C_4)$alkylamino, a cyano, a trifluoromethyl radical, a trifluoromethoxy radical, a group $S(O)_n$Alk, a $(C_1-C_4)$alkylcarbonyl group; or from a phenyl, phenoxy, pyrrolyl, imidazolyl, pyridyl or pyrazolyl radical, the said radicals being unsubstituted or substituted one or more times with a $(C_1-C_4)$alkyl;

an unsubstituted benzyl or a benzyl mono- or disubstituted on the phenyl with substituents independently chosen from a halogen atom, a $(C_1-C_4)$alkyl, a $(C_1-C_4)$alkoxy or a trifluoromethyl radical, or alpha-substituted with one or two identical or different groups chosen from a $(C_1-C_4)$alkyl and a $(C_3-C_7)$cycloalkyl;

an unsubstituted phenethyl or a phenethyl mono- or disubstituted on the phenyl with substituents independently chosen from a halogen atom, a $(C_1-C_4)$alkyl, a $(C_1-C_4)$alkoxy and a trifluoromethyl radical;

a benzhydryl; a benzhydrylmethyl;

an aromatic heterocyclic radical chosen from a pyrrolyl, an imidazolyl, a furyl, a thienyl, a pyrazolyl or an indolyl, which is unsubstituted or substituted one or more times with substituents independently chosen from a halogen atom, a $(C_1-C_4)$alkyl and a trifluoromethyl radical;

$R_2$ represents a hydrogen atom or a $(C_1-C_3)$alkyl;

$R_3$ represents a $(C_1-C_5)$alkyl or a $(C_3-C_7)$cycloalkyl;

$R_4$ represents an unsubstituted phenyl or a phenyl mono-, di- or trisubstituted with substituents chosen independently from a halogen atom, a $(C_1-C_4)$alkyl, a $(C_1-C_4)$alkoxy, a trifluoromethyl radical and a group $S(O)_n$Alk;

$R_5$ represents an unsubstituted phenyl or a phenyl mono-, di-, or trisubstituted with substituents chosen independently from a halogen atom, a $(C_1-C_4)$alkyl, a $(C_1-C_4)$alkoxy, a trifluoromethyl radical and a group $S(O)_n$Alk;

$R_6$ represents a hydrogen atom or a $(C_1-C_3)$alkyl;

n represents 0, 1 or 2; and

Alk represents a $(C_1-C_4)$alkyl, or a hydrate or a solvate thereof.

2. The compound of formula (I) according to claim 1 wherein —X— represents a —CO— radical and the substituents $R_1$ to $R_5$ are as defined for the compounds of formula (I) in claim 1;
or a hydrate or a solvate thereof.

3. The compound of formula (I) according to claim 1 wherein —X— represents an —SO$_2$— radical and the substituents $R_1$ to $R_5$ are as defined for the compounds of formula (I) in claim 1;
or a hydrate or a solvate thereof.

4. The compound of formula (I) according to claim 1 wherein —X— represents a radical —CON($R_6$)— and the substituents $R_1$ to $R_6$ are as defined for the compounds of formula (I) in claim 1;
or a hydrate or a solvate thereof.

5. The compound of formula (I) according to claim 1 wherein —X— represents a —COO— radical and the substituents $R_1$ to $R_5$ are as defined for the compounds of formula (I) in claim 1;
or a hydrate or a solvate thereof.

6. The compound of formula (I) according to claim 1 wherein —X— represents an —SO— radical and the substituents $R_1$ to $R_5$ are as defined for the compounds of formula (I) according to claim 1;
or a hydrate or a solvate thereof.

7. The compound of formula (I) according to claim 1 wherein —X— represents a —CO— group, an —SO$_2$— group; an —SO— group or a —CON(CH$_2$CH$_3$)— group;

$R_1$ represents:
a 1-ethylpropyl; a 1-methylpentyl; a tert-butyl; an ethyl; a cycloheptyl; a 1-methylcyclopropyl;
a 3-(trifluoromethyl)phenyl; a 4-(trifluoromethyl)phenyl;
$R_2$ represents a hydrogen atom;
$R_3$ represents a methyl;
$R_4$ represents a 4-bromophenyl; a 4-chlorophenyl; and
$R_5$ represents a 2,4-dichlorophenyl;
or a hydrate or a solvate thereof.

8. The compound of formula (I) according to claim 1 wherein:
X represents a —CO— group or an —SO$_2$— group;
$R_1$ represents:
a 1-ethylpropyl; a 1-methylpentyl;
a cycloheptyl;
a 3-(trifluoromethyl)phenyl;
$R_2$ represents a hydrogen atom;
$R_3$ represents a methyl;
$R_4$ represents a 4-bromophenyl; and
$R_5$ represents a 2,4-dichlorophenyl;
or a hydrate or a solvate thereof.

9. The compound of formula (I) according to claim 1, chosen from:
N-[[4-(4-bromophenyl)-5-(2,4-dichlorophenyl)-3-methyl-2-thienyl]methyl]-2-ethylbutanamide;
N-[[4-(4-bromophenyl)-5-(2,4-dichlorophenyl)-3-methyl-2-thienyl]methyl]cycloheptanecarboxamide;
N-[[4-(4-bromophenyl)-5-(2,4-dichlorophenyl)-3-methyl-2-thienyl]methyl]-3-(trifluoromethyl)benzenesulfonamide;
N-[[4-(4-bromophenyl)-5-(2,4-dichlorophenyl)-3-methyl-2-thienyl]methyl]-2-methylhexanamide;
N-[[4-(4-chlorophenyl)-5-(2,4-dichlorophenyl)-3-methyl-2-thienyl]methyl]-2,2-dimethylpropanamide;
N-[[4-(4-chlorophenyl)-5-(2,4-dichlorophenyl)-3-methyl-2-thienyl]methyl]-2-methylbutanamide;
N-[[4-(4-chlorophenyl)-5-(2,4-dichlorophenyl)-3-methyl-2-thienyl]methyl]-1-methylcyclopropanecarboxamide;
N-[[4-(4-bromophenyl)-5-(2,4-dichlorophenyl)-3-methyl-2-thienyl]methyl]-4-(trifluoromethyl)benzamide;
N-[[4-(4-chlorophenyl)-5-(2,4-dichlorophenyl)-3-methyl-2-thienyl]methyl]-2- methylpropane-2-sulfinamide;
N-[[4-(4-chlorophenyl)-5-(2,4-dichlorophenyl)-3-methyl-2-thienyl]methyl]-2-methylpropane-2-sulfonamide;
3-[[4-(4-chlorophenyl)-5-(2,4-dichlorophenyl)-3-methyl-2-thienyl]methyl]-1,1-diethylurea;
or a hydrate or a solvate thereof.

10. A process for preparing a compound of formula (I) according to claim 1, comprising:
treating a compound of formula (II):

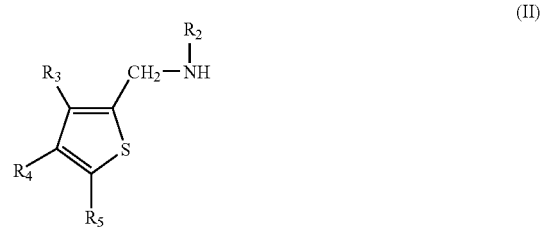

in which $R_2$, $R_3$, $R_4$ and $R_5$ are as defined for a compound of formula (I) in claim 1,
either with an acid or a functional derivative thereof, said acid is of formula (III):

in which $R_1$ is as defined for a compound of formula (I) in claim 1, when a compound of formula (I) is to be prepared in which —X— represents a —CO— group;

or with a sulfonyl halide of formula (IV):

Hal-SO$_2$—R$_1$ (IV)

in which R$_1$ is as defined for a compound of formula (I) in claim 1 and Hal represents a halogen atom, when a compound of formula (I) is to be prepared in which —X— represents an —SO$_2$— group;
or with a haloformate of formula (V):

HalCOOAr (V)

in which Hal represents a halogen atom and Ar represents a phenyl or a 4-nitrophenyl, to give an intermediate compound of formula (VI):

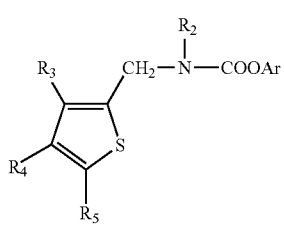

(VI)

in which R$_2$, R$_3$, R$_4$ and R$_5$ are as defined for a compound of formula (I) in claim 1,
which is then reacted with an amine of formula (VII):

HN(R$_6$)R$_1$ (VII)

in which R$_1$ and R$_6$ are as defined for a compound of formula (I) in claim 1, when a compound of formula (I) is to be prepared in which —X— represents a group —CON(R$_6$)—;
or with a haloformate of formula (XXIV):

HalCOO—R$_1$ (XXIV)

in which Hal represents a halogen atom and R$_1$ is as defined for a compound of formula (I) in claim 1, when a compound of formula (I) in claim 1 is to be prepared in which —X— represents a —COO— group,
or with a sulfinyl halide of formula (XXV):

Hal-SO—R$_1$ (XXV)

in which R$_1$ is as defined for a compound of formula (I) in claim 1 and Hal represents a halogen atom, when a compound of formula (I) is to be prepared in which —X— represents an —SO— group.

11. A pharmaceutical composition comprising a compound of formula (I) according to claim 1 or a hydrate or a solvate thereof in combination with at least one pharmaceutically acceptable excipient.

12. A pharmaceutical composition comprising a compound of formula (I) according to claim 2 or a hydrate or a solvate thereof in combination with at least one pharmaceutically acceptable excipient.

13. A pharmaceutical composition comprising a compound of formula (I) according to claim 3 or a hydrate or a solvate thereof in combination with at least one pharmaceutically acceptable excipient.

14. A pharmaceutical composition comprising a compound of formula (I) according to claim 4 or a hydrate or a solvate thereof in combination with at least one pharmaceutically acceptable excipient.

15. A pharmaceutical composition comprising a compound of formula (I) according to claim 5 or a hydrate or a solvate thereof in combination with at least one pharmaceutically acceptable excipient.

16. A pharmaceutical composition comprising a compound of formula (I) according to claim 6 or a hydrate or a solvate thereof in combination with at least one pharmaceutically acceptable excipient.

17. A pharmaceutical composition comprising a compound of formula (I) according to claim 7 or a hydrate or a solvate thereof in combination with at least one pharmaceutically acceptable excipient.

18. A pharmaceutical composition comprising a compound of formula (I) according to claim 8 or a hydrate or a solvate thereof in combination with at least one pharmaceutically acceptable excipient.

19. A pharmaceutical composition comprising a compound of formula (I) according to claim 9 or a hydrate or a solvate thereof in combination with at least one pharmaceutically acceptable excipient.

* * * * *